United States Patent [19]

Mar

[11] Patent Number: 5,483,022
[45] Date of Patent: Jan. 9, 1996

[54] IMPLANTABLE CONDUCTOR COIL FORMED FROM CABLED COMPOSITE WIRE

[75] Inventor: Craig E. Mar, Fremont, Calif.

[73] Assignee: Ventritex, Inc., Sunnyvale, Calif.

[21] Appl. No.: 226,180

[22] Filed: Apr. 12, 1994

[51] Int. Cl.[6] .................................................. H01B 5/10
[52] U.S. Cl. ................................ 174/128.1; 174/119 R; 174/126.2; 174/130
[58] Field of Search ................................ 174/119 R, 69, 174/128.1, 130, 126.2, 128.2; 607/116, 119, 122, 142

[56] References Cited

U.S. PATENT DOCUMENTS

| | | | |
|---|---|---|---|
| 2,978,530 | 4/1961 | Braeckman | 174/34 |
| 3,333,045 | 7/1967 | Fisher et al. | 174/20 |
| 4,514,589 | 4/1985 | Aldinger et al. | 174/119 R |
| 4,640,983 | 2/1987 | Comte | 174/119 |
| 4,860,446 | 8/1989 | Lessar et al. | 29/898 |
| 5,246,014 | 9/1993 | Williams et al. | 607/122 |
| 5,303,704 | 4/1994 | Molacek | 128/642 |
| 5,330,521 | 7/1994 | Cohen | 607/122 |
| 5,358,517 | 10/1994 | Pohndorf et al. | 607/116 |
| 5,360,442 | 11/1994 | Dahl et al. | 607/129 |

FOREIGN PATENT DOCUMENTS

| | | |
|---|---|---|
| 2820867 | 5/1978 | Germany. |
| 8004757 | 8/1980 | Netherlands. |

OTHER PUBLICATIONS

"Precious Metal Clad Wire for use in Connectors", Gallant, R., et al., 19th Annual Connector and Interconnection Technology Proceedings, 1986, pp. 192–201.

"Stranded Wire Helical Springs", Clark, H. H., Spring Design and Application, edited by Nocholas P. Chironis, McGraw–Hill Book Company, Inc., 1961, pp. 92–96.

"Mechanics of Materials", Mechanical Engineering Review Manual, 7th ed., Michael R. Lindeburg, 1984, pp. 14-2-14-9.

"DFT Drawn Filled Tubing", Fort Wayne Metals Research Products, Corp., Jul. 1989.

"A Study of the Fatigue Properties of Small Diameter Wires used in Intramuscular Electrodes", Journal of Biomedical Materials Research, vol. 25, 1991, pp. 589–608.

*Primary Examiner*—Morris H. Nimmo
*Attorney, Agent, or Firm*—Steven M. Mitchell; M. Elizabeth Bush; Mark J. Meltzer

[57] ABSTRACT

An implantable lead conductor comprises at least one helical coil formed from at least one electrical cable. Each cable is formed from several wires twisted in a ropelike configuration with at least some of the wires being helically wound around a central axis of the cable. Each wire is a composite comprising a core of a first material and a coveting of a second material, with all adjacent wires belonging to the same cable in uninsulated contact with each other. Preferably, the core material is highly conductive, and the covering material is strong and biocompatible. The helical coil has a lumen for insertion of a stylet to facilitate insertion through a vein.

9 Claims, 3 Drawing Sheets

5,483,022

IMPLANTABLE CONDUCTOR COIL FORMED FROM CABLED COMPOSITE WIRE

FIELD OF THE INVENTION

The present invention relates generally to cardiac stimulation devices, and more specifically to a lead conductor with improved flexibility, fatigue resistance, corrosion resistance, and electrical conductivity for use with an implantable defibrillator.

BACKGROUND OF THE INVENTION

The human body imposes stringent requirements on electrical conductors that are implanted in it. Cardiac pacing and defibrillation leads are subjected to flexure with every heartbeat which total approximately 100,000 per day or over 30 million a year. Conductors and their insulators in parts of the leads that are remote from the heart often undergo stresses of various kinds during body movement. A living body also constitutes a site that is chemically and biologically hostile to anything that invades it. Therefore, it is not surprising that with prior art leads, the conductors and insulation deteriorated in a period that was shorter than desired for a device that requires major surgery to correct.

With the advancement of implantable defibrillator and pacemaker technology, more electrodes, and consequently more conductors are used to provide sensing, pacing, defibrillation, and other functions Because of the increase in number of conductors, it is important that their individual size does not increase, and preferably, that it decrease. Defibrillator conductors in particular are required to carry much larger currents than other types of conductors, and therefore must have very low resistances over their lengths. For example, a defibrillator conductor may carry 35 amperes or more of current, whereas a pacing lead may carry only about 100 milliamperes. Because defibrillators are usually implanted in the abdominal region rather than in the typical pectoral pacemaker implant site, defibrillator leads must usually be longer than pacemaker leads. The defibrillator conductor must be about 4 ohms or less over a length of up to about 110 centimeters; the pacemaker conductor may be closer to 40 ohms, and as much as about 200 ohms, over about 60 centimeters. Therefore, a small diameter, low resistance conductor with a high fatigue life in the body is desired.

Unfortunately, the materials with the highest conductivities, such as copper, silver, and gold, also tend to have low yield strength, and consequently low fatigue life. Also unfortunate is the fact that for coil construction, the variables that increase conductivity also decrease fatigue life; that is, conductivity increases for increased wire diameter, increased pitch, and decreased mean coil diameter, whereas fatigue life increases for decreased wire diameter, decreased pitch, and increased mean coil diameter.

In U.S. Pat. No. 4,640,983, which is incorporated herein by reference, Comte describes a conductor device comprising at least one spiral formed from a plurality of electrical conductors arranged to form a single-layer winding, wherein each of the conductors is formed from several wires bundled in a ropelike configuration, and wherein each wire consists of the same material over its entire cross section. Comte attempts to solve tho problem of combining strength and conductivity by combining different material wires in a conductor thus having some wires of each of two materials, one material being strong arid the other one being highly conductive. As described, if the sheathing which normally protects the wires is damaged, the wires of both materials would come in contact with blood or other cells and tissues of the patient's body. Silver and copper are the most likely candidates for the highly conductive material; however, they are not biocompatible and will readily corrode in body fluids.

Drawn brazed stranded (DBS) material has been used in the past to make strong wire having low electrical resistance for use in cable or coil. This material is formed from six segments of a strong material such as 316L stainless steel or MP35N cobalt-nickel-chromium-molybdenum alloy which enclose a core of silver; the segments and core are brazed together with silver securely connecting all of the segments, then drawn down to the final wire diameter. This wire has a tendency to kink and is difficult to wind into a uniform helical coil. Nonuniformities, and especially kinks, render the wire prone to fatigue. Also, because silver is used to braze the materials together, silver remains exposed on the outside of the wire. Because silver has been implicated in the degradation of polyurethane materials, which are often used as insulators in implantable products, the choice of insulating materials is limited if DBS is used. Furthermore, any breach in an alternative insulating material such as silicone rubber would expose the silver to body fluids, subjecting it to corrosion. Because silver extends from the wire exterior into its interior, corrosion of silver in brazed joints could lead to complete failure of the wire.

SUMMARY OF THE INVENTION

The present invention is directed to a biomedical conductor device which utilizes a plurality, preferably seven, one core and six outside, drawn filled tubing (DFT) or other composite wires which are twisted together to form a cable. One or more of these cables are then spiral wound in a helical structure to form a lead conductor coil. Each of the composite wires comprises a core of a first material surrounded by a covering of a second material. All adjacent wires belonging to the same cable are in uninsulated contact with each other.

An object of the invention is to provide an implantable lead with improved flexibility, fatigue resistance, corrosion resistance, and electrical conductivity.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
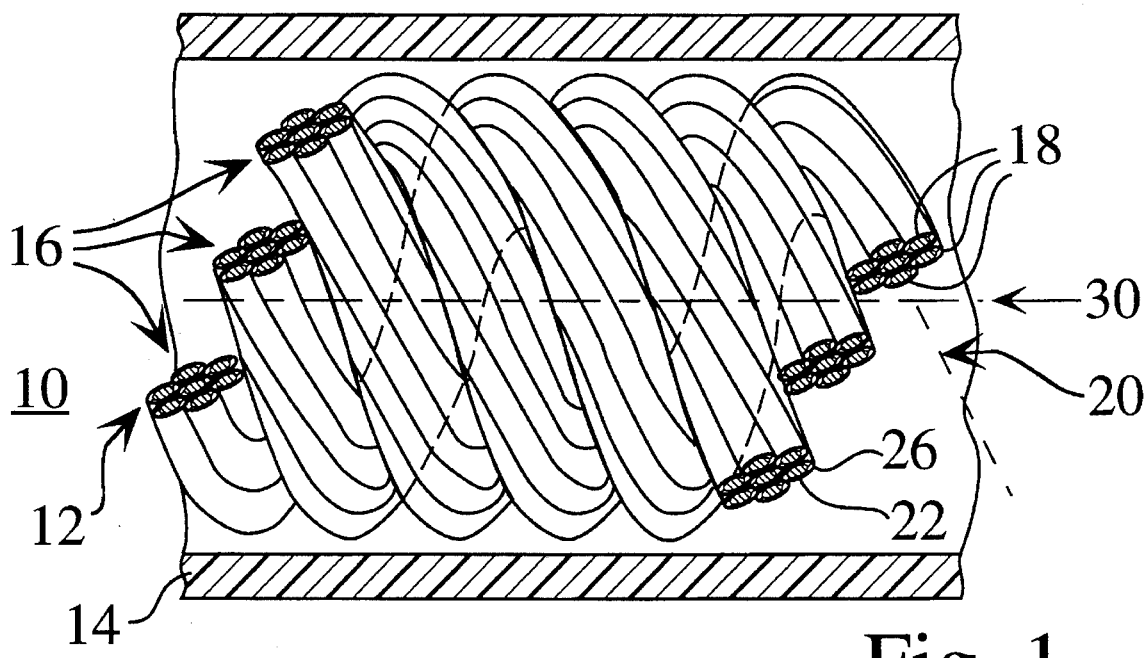
FIG. 1 is a longitudinal section of a lead conductor, wherein the insulative sheath is shown in section and the coil is shown in front view.

FIG. 1 is a longitudinal section of a conductor device 10, having a coil 12 shown in front view and an insulative sheath 14 shown in section. Helical coil 12 is formed from at least one, and preferably not more than 6, electrical cables 16. Coil 12 is about 0.43 to 3.8 mm in outer diameter, and preferably about 0.5 to 2 mm. Cable 16 is about 0.038 to 0.76 mm in thickness, and preferably about 0.076 to 0.23 mm. Each cable 16 is formed from several wires 18 twisted in a ropelike configuration with the wires 18 being helically wound around a central axis 20 of the cable. Two to nineteen wires 18 may form each cable 16, and preferably three to seven. Each wire 18 is a composite and comprises a core 22 of a first material and a covering 26 of a second material. Each wire 18 is about 0.012 to 0.25 mm in diameter, and about 0.025 to 0.076 mm in the preferred embodiment. The core 22 comprises about 10% to 60% of the wire by volume, and about 20% to 45% in the preferred embodiment. Such wire in the form of Drawn filled tubing (DFT) is available from Fort Wayne Metals Research Products Corporation, and is a composite having a tubing of one metal filled with a core of another metal, then drawn down into a wire. Order processes such as cladding may be used to produce a wire having a core with a covering material to form a similar structure, such as that used by Anomet Products Inc., Shrewsbury, Mass. All adjacent wires belonging to the same cable are in uninsulated contact with each other. The helical coil 12 has a lumen 30 for insertion of a stylet (not shown) to facilitate insertion through a vein. The first material comprising core 22 has greater electrical conductivity than the second material of covering 26, and the second material has a greater breaking strength and better biocompatibility than the first material. In the preferred embodiment, the core material is silver, and the covering material is MP35N, which is a nickel-cobalt-chromium-molybdenum alloy. In a preferred embodiment, every one of the wires 18 is formed of the same said first and second materials, Alternatively, some wires may be formed of a different combination of materials.

A substantial advantage of the coiled cabled conductor devices of this invention is that they are not plastically deformed down to very small radii of curvature. Accordingly, if, as can happen, e.g., during implantation, a lead is temporarily bent with such a small radius of curvature, no permanent or lasting deformation remains after the deforming force is removed. Moreover, the coiled cables are also elastically expandable in their longitudinal direction and are not sensitive to torsion.

This composite wire provides several advantages over other composite and solid wire forms. Unlike DBS, because the core is completely surrounded by biocompatible material, it is not critical that the core be biocompatible. Also, the weakness of the core is mitigated by the strong outer material completely holding it together, even if microcracks were to form in it. Even if several wires were to completely break through, the resistance would not be substantially increased because the interruptions are bridged by the rest of the wires.

Bending stress, or flexure stress, varies with position throughout the cross section of the wire. It is zero at the center, but it increases with distance from the center. Since the maximum stress occurs at the surface of the wire, using a composite material with the strongest material on the outside provides significant advantage by allowing greater stress without permanent deformation. Since minimal stress occurs in the core of the wire, it is less important that the core material be strong.

Figure 2:
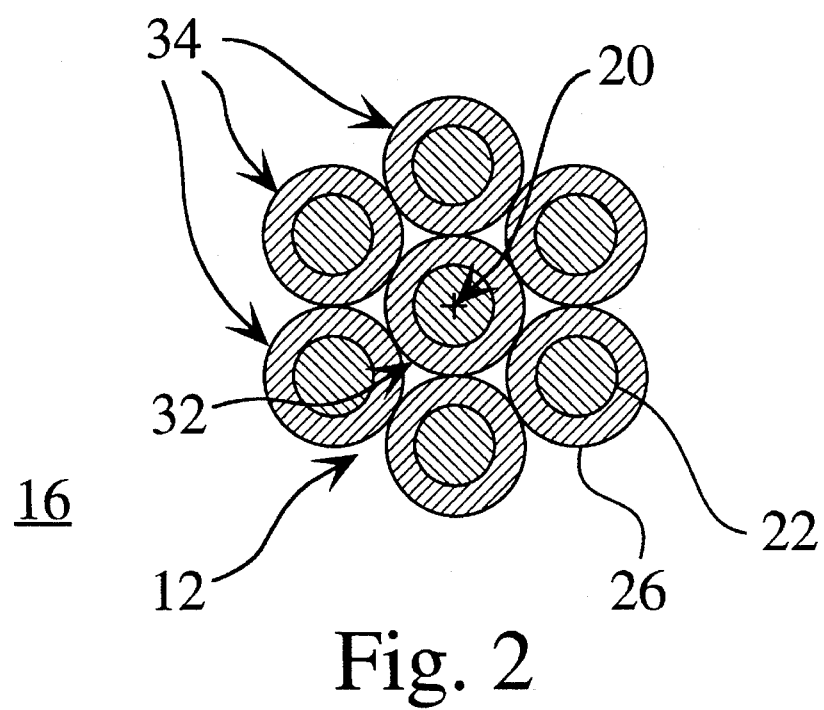
FIG. 2 is a cross section through a cable.

FIG. 2 is a cross section through a cable 16. The cable 16 has a central filament wire 32, which is enclosed by six outer wires 34. The central filament wire 32 is shown to have the same diameter as the other wires, but may alternatively have a greater diameter than the other wires 34 extending around the central filament wire 32. Each wire comprises a core 22 made of a highly conductive material, completely surrounded by a covering 26 of a strong, biocompatible material, to provide biocompatibility, corrosion resistance, tensile and bending strength, fatigue resistance, and electrical conductivity.

Figure 3:
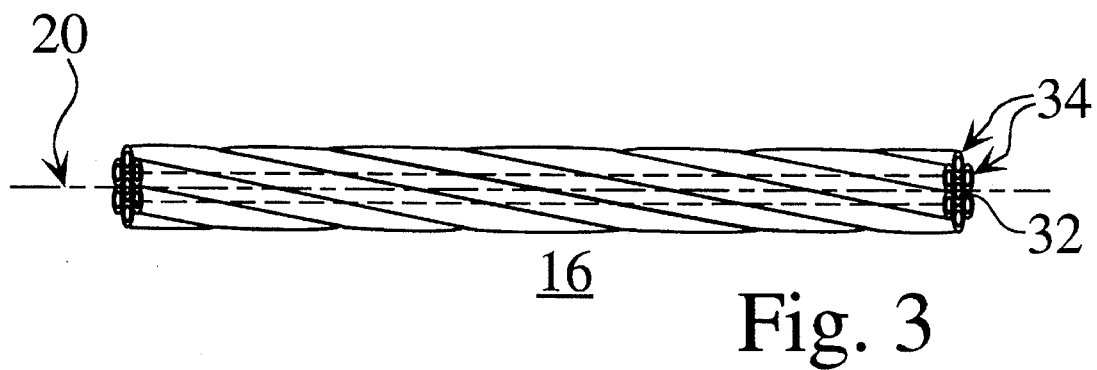
FIG. 3 is a view of a single, uncoiled cable.

FIG. 3 is a view of a single, uncoiled cable 16 having a central axis 20. The cable 16 has a central filament wire 32 which is enclosed by six outer wires 34.

Figure 4:
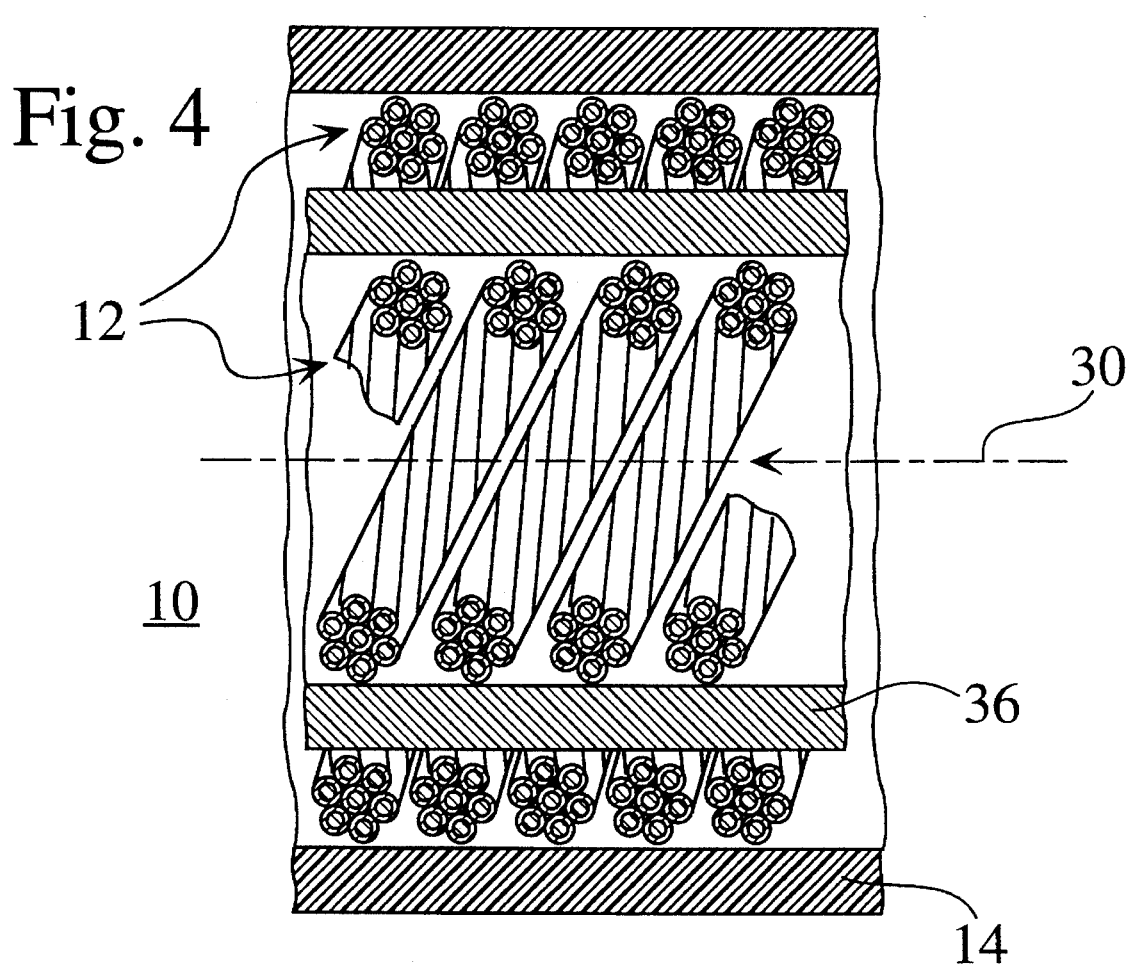
FIG. 4 is a schematized longitudinal section through a variant of a conductor device with two coils.

FIG. 4 is a schematized longitudinal section through a conductor device 10 with two helical coils 12, one of them enclosing the other coaxially, and separated by an electrically insulating polymeric material 36. This provides a lumen for insertion of a styler to stiffen the conductor device during implantation, and allows conductors for two separate electrodes and/or lead connectors to occupy less space than in a side-by-side configuration. In addition, by making the coils 12 coaxial, the structure remains radially symmetrical, which increases fatigue life and improves handling during implantation.

Figure 5:
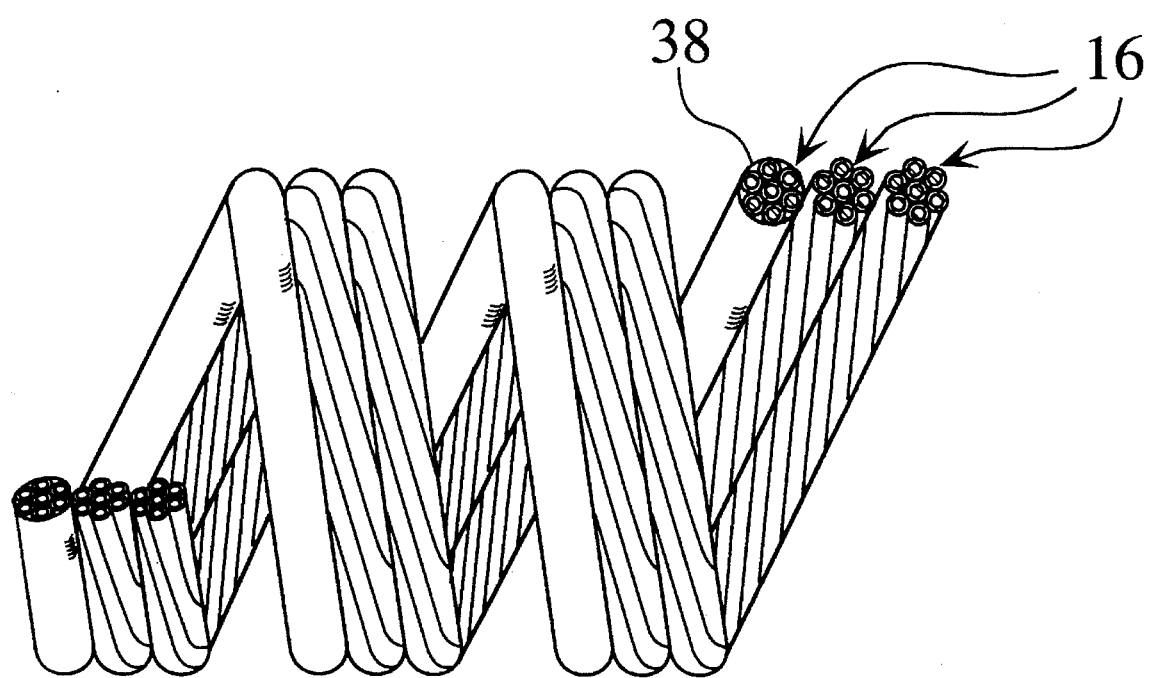
FIG. 5 is a schematized longitudinal section through a variant of a conductor device with cables which are insulated from each other.

FIG. 5 is a schematized longitudinal section through a conductor device 10 with three cables 16 wherein one cable is insulated from the other two cables by a covering of electrically insulating polymeric material 38. Alternatively, any number of cables may be insulated from any other number of cables to provide sufficient conductivity and redundancy for both sets of cables. As another alternative, three or more cables or sets of cables may be mutually insulated by a covering of electrically insulating polymeric material 38, to provide conductors to three or more separate electrodes and/or lead connectors. This structure provides a stylet lumen and keeps the structure radially symmetrical, while allowing conductors for two separate electrodes and/ or lead connectors to occupy even less space than in the embodiment of FIG. 4.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A biomedical conductor device, for at least partial insertion in a human or animal body, comprising:

at least one helical coil formed from at least one electrical cable, said cable being formed from a plurality of wires twisted in a ropelike configuration with at least a part of said wires being helically wound around a central axis of said cable so that the wires belonging to said cable are held together and are movable with respect to each other within certain limits; and each of said wires comprising a core of a first material, said core being surrounded by a covering of a second material over the length of said core, wherein all adjacent wires belonging to the same cable are in uninsulated contact with each other.

2. A conductor device according to claim 1 comprising a first and a second of said helical coils, said first coil enclosing said second coil coaxially, wherein said first and second coils are separated by an electrically insulating polymeric material.

3. A conductor device according to claim 1, wherein said cable has at least one central filament wire, said central filament wire being enclosed by at least one surrounding wire.

4. A conductor device according to claim 3, wherein said central filament wire is enclosed by six of said surrounding wires.

5. A conductor device according to claim 3, wherein said central filament wire has a greater diameter than said at least one surrounding wire extending around said central filament wire.

6. A conductor device according to claim 1, wherein said second material has a greater breaking strength and better biocompatibility than said first material, and wherein said first material has greater electrical conductivity than said second material.

7. A conductor device according to claim 1, wherein every one of said several wires is formed of the same said first and second materials.

8. A conductor device according to claim 1, wherein at least one of said electrical cables is separated from at least one other of said electrical cables by a covering of electrically insulating polymeric material.

9. A conductor device according to claim 1, wherein said helical coil is formed to define at a central inner part thereof a cavity open at one end for insertion therein of a flexible stylet to facilitate insertion of said conductor device into said human or animal body.

* * * * *